US00PP18959P2

(12) United States Plant Patent
Sheehan

(10) Patent No.: US PP18,959 P2
(45) Date of Patent: Jun. 17, 2008

(54) GRAPEVINE 'SHEEGENE-10'

(50) Latin Name: *Vitis vinifera*
Varietal Denomination: Sheegene-10

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 11/708,768

(22) Filed: Feb. 20, 2007

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Baker Manock & Jensen, PC; Eric C. Cole

(57) ABSTRACT

A new and distinct variety characterized by medium to large, red-colored seedless grapes with a very good flavor that ripen in late July, approximately two weeks later than the Flame Seedless Grape (unpatented), when grown in the San Joaquin Valley of Central California. The grapes of this new variety are produced on strong woody branches and stems and are well adapted to commercial handling.

1 Drawing Sheet

Latin name of the genus and species of the plant claimed: The claimed plant relates to a new and distinct variety of *Vitis vinifera* to be known as 'Sheegene-10'.

Variety denomination: This invention relates to a new discovery and asexual reproduction of a new variety of *Vitis vinifera.* The new variety was first hybridized by Timothy P. Sheehan of Porterville, Calif., in late Spring 2000. The pollen parent is 'Princess' (unpatented) and the seed parent is 'Red Globe' (U.S. Plant Pat. No. 4,787). The new variety was asexually propagated in the dormant season of 2003, grafted on 'Harmony', virus-free rootstock near Fowler, Calif. Five vines were planted at that time in a *Vitis vinifera* variety block located near Fowler, Calif., on the west side of Thompson Road, north of Adams Road. The red-colored seedless grapes produced by the new variety are medium to large in size and mature approximately two weeks later than 'Flame Seedless' (unpatented). The new variety has been shown to maintain its distinguishing characteristics through asexual propagation.

BACKGROUND OF THE INVENTION

The present invention relates to a new and distinct variety of grape which will hereinafter be denominated as 'Sheegene-10' and more particularly as a grapevine which produces a medium to large, red-colored seedless grape that matures in late July in the San Joaquin Valley of Central California. The new invention resembles 'Flame Seedless' (unpatented) but it produces a larger grape with a very sweet flavor, and matures approximately two weeks later.

SUMMARY OF THE INVENTION

The 'Sheegene-10' is characterized by producing a medium to large, red-colored seedless grape with very good flavor that is mature for harvesting and shipment in late July in the San Joaquin Valley of Central California. The new variety of grape can be compared to 'Flame Seedless' (unpatented) but the grapes are larger and mature about two weeks later, among other distinguishing characteristics.

BRIEF DESCRIPTION OF THE DRAWING

The accompanying drawing is a color photograph of the grapes produced by the subject variety; several leaves are displayed as well as a typical section of the vine. Across the top of the color photograph on the left is a small shoot with leaves and tendrils, a secondary growth small cluster and berries; in the center is a grape leaf and petiole; and to the right is a display of the topside of a leaf. Across the middle of the color photograph on the left is a major grape cluster; in the center is a secondary growth cluster; and to the right are small shoot leaves and tendrils. Across the bottom of the color photograph on the left are four grapes cut in half longitudinally as well as horizontally displaying the flesh and shape; just above is a leaf and petiole displaying the bottom surface of the leaf; and to the right is a section of mature cane with leaves and nodes.

DETAILED BOTANICAL DESCRIPTION

Referring more to the horticultural description of the new and distinct variety of grapevine, the following description has been observed under the ecological conditions prevailing at the origin vineyard that is located near Fowler, Calif. in the San Joaquin Valley of Central California. All major color descriptions are by reference to the Dictionary of Color by Maerz and Paul, First Edition, published in 1930. Common color names are also used in several instances.

VINE
Size: Medium to large for a four year old vine.
Vigor: Very good.
Chilling requirements: Normal for grapevines in the San Joaquin Valley of Central California.
Figure: With wide cordons forming a "T" shaped figure.
Production capacity: Good.
Regularity of bearing: Regular.
TRUNK
Size: Medium to large; 22.86 cm (9 inches) in circular "S" shape.
Surface texture: Rough, shaggy.
Color of bark: Pl.7 C7 Bonito Euscous +.
*Mature canes.*—Color: Pl.13 Li Buckthorn Br. Sumac.
Nodes: Five nodes on cane.
Length between nodes: 3 to 4 inches (7.6 cm to 10.2 cm).
*Lenticels.*—Number: None.

Shoot contour: Drooping.
*Tendrils.*—Number: One at nodes.
*Tendrils.*—Size: Variable; 45 to 90 mm (1.77 to 3.54 inches).
Tendrils form: Bifurcate.
*Tendrils.*—Texture: Firm to woody.
Bud shape: Triangular.
Bud size: 8 to 10 mm (0.31 to 0.39 inches) in length; 8 to 10 mm (0.34 to 0.39 inches) in width.
Buds fruitfulness: Very good.
BRANCHES
Size: Medium to large: 4½ inches (11.03 cm) in circumference.
Surface texture: Slightly rough.
Cordons: 29 to 33 inches (73.66 to 83.82 cm) from trunk.
*Color.*—One Year or Older Wood: Pl.6 18 Slate V.
*Color.*—Immature Branches: Pl.20 K1 Russet green.
LEAVES
Size: Medium to large.
Density: Dense.
Average length: 15.0 to 15.5 cm (5.91 to 6.10 inches).
Average width: 14.7-17.0 cm (5.79 to 6.69 inches).
Shape: Pentagonal.
*Texture.*—Upper surface: Smooth.
*Texture.*—Lower surface: Smooth.
*Color.*—Upward Disposed Surface: Pl.23 J9 Polo green.
*Color.*—Downward Disposed Surface: Pl.20 K6 Piquant gr.
*Color.*—Leaf Vein: Pl.17 I6 Viridine gr.
Marginal form: Slightly undulated.
*Leaf vein.*—Thickness: 2 mm (0.79 inches).
Leaf margin: Toothed.
*Glandular characteristics.*—0.
Petiole size: Large.
Petiole length: 11.1 to 14.7 cm (4.37 to 5.79 inches).
Petiole thickness: 4 mm (0.16 inches).
*Petiole.*—Color: Pl.17 16 Viridine gr.
Petiole sinus form: Upside down "U" shape.
Lobes: Four (average).
Tooth size: 10 to 12 mm (0.39 to 0.47 inches) in length; 10 to 12 mm (0.39 to 0.47 inches) in width.
*Tooth.*—Number: Four large between nodes (11 to 13 small).
*Tooth.*—Shape: Convex.
FRUIT
Solids: 20.1° Brix.
Acids: 0.5.
Sugar/acid ratio: 40.2.
Juice pH: 3.24.
Seeds: None.
Capstem pedicel (average): 10 mm (0.39 inches).
Berry weight: 5 grams.
Juice color: Pl.1 D7 Rose Breath.
Cluster size: Large.
Cluster average length: 24 to 25 cm (9.45 to 9.84 inches).
Cluster average diameter: 12 to 13 cm (0.47 to 0.50 inches).
Cluster weight: 624.8 grams (1 lb. 6 oz.).
Cluster compactness: Compact.
Cluster form: Conical.
Stem: Generally variable; 25 to 70 mm (0.98 to 2.75 inches).
*Stem.*—Caliper: 4 to 8 mm (0.16 to 0.31 inches).
Berry size: Medium to Large.
Berry shape: Ovate.
Berry number: Approximately 145 per bunch.
*Berry size.*—Average Dimension along Longitudinal Axis: 25 to 28 mm (0.98 to 1.10 inches).
*Berry size.*—Average Dimension along Transverse Axis: 18 to 19 mm (0.71 to 0.75 inches).
SKIN
Skin thickness: Medium.
Texture: Semi-tough.
Tendency to crack: None known.
Blush color: Pl. 7 E6 Canyon.
Ground color: Pl.5 C7 Misty Morn.
Pulp: Ranging from clear to Pl.7 B9 Kaffa Hamstead Brown.
Lenticels: None.
FLESH
Flesh color: Pl.6 L8 Mascara.
Juice production: Good.
Flavor: Very good.
Aroma: Mild.
Texture: Firm.
Ripening: Even.
Eating quality: Very good.
Use: Fresh market.
Keeping quality: Good.
Resistance to disease: Unknown.
Harvesting: Late July to August.
Shipping and handling quality: Very good.

Having thus described and illustrated our new variety of grapevine, we claim:

1. A new variety of grapevine to be known as Sheegene-10 and parts thereof, substantially as illustrated and described, characterized principally by its production of medium to large, red-colored seedless grapes, that mature approximately two weeks later in the season of ripening than does the Flame Seedless Grape (unpatented) which it resembles.

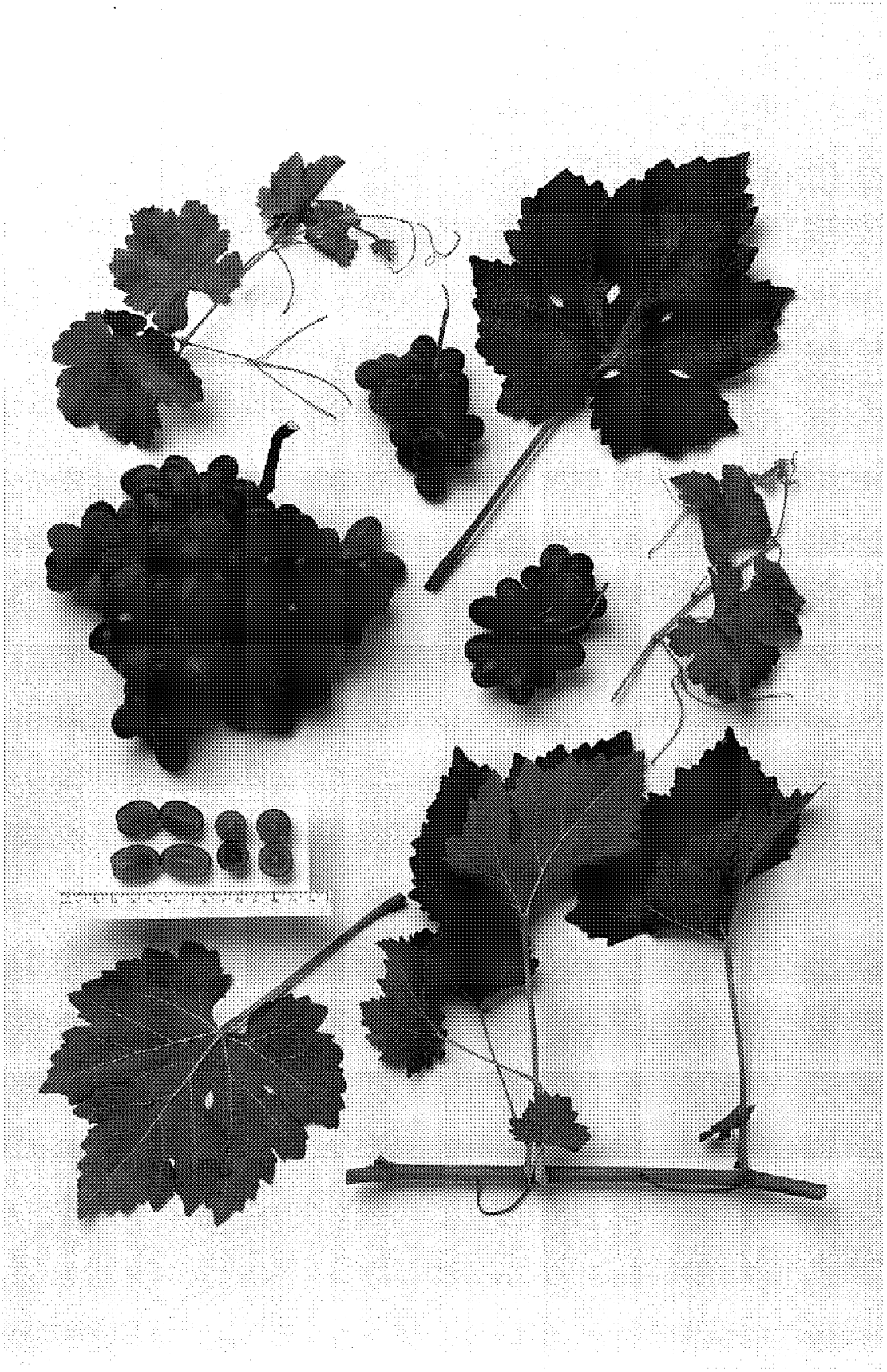

* * * * *